(12) United States Patent
Schneider et al.

(10) Patent No.: US 9,272,096 B2
(45) Date of Patent: Mar. 1, 2016

(54) DRIVE ASSEMBLY FOR A DRUG DELIVERY DEVICE AND CORRESPONDING DRUG DELIVERY DEVICE

(75) Inventors: Christiane Schneider, Frankfurt am Main (DE); Tobias Stever, Frankfurt am Main (DE); Michael Harms, Frankfurt am Main (DE); Ulrik Jakobi, Frankfurt am Main (DE); Ngoc-Jane Lam, Frankfurt am Main (DE); Torsten Kraft, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 25 days.

(21) Appl. No.: 14/114,903

(22) PCT Filed: May 4, 2012

(86) PCT No.: PCT/EP2012/058181
§ 371 (c)(1),
(2), (4) Date: Oct. 30, 2013

(87) PCT Pub. No.: WO2012/152667
PCT Pub. Date: Nov. 15, 2012

(65) Prior Publication Data
US 2014/0074042 A1     Mar. 13, 2014

(30) Foreign Application Priority Data
May 6, 2011   (EP) .................................. 11165045

(51) Int. Cl.
*A61M 5/315* (2006.01)
*A61M 5/24* (2006.01)

(52) U.S. Cl.
CPC ....... *A61M 5/31543* (2013.01); *A61M 5/31551* (2013.01); *A61M 5/31585* (2013.01);
(Continued)

(58) Field of Classification Search
CPC .......... A61M 2005/2488; A61M 5/24; A61M 5/31543; A61M 5/31551; A61M 5/31585
USPC .......... 604/208–211, 218, 220, 224, 228, 233
See application file for complete search history.

(56) References Cited

U.S. PATENT DOCUMENTS 5,304,152 A * 4/1994 Sams ................ A61M 5/31553
604/207
8,491,538 B2    7/2013 Kohlbrenner et al.
(Continued)

FOREIGN PATENT DOCUMENTS

WO    2006058061 A1    6/2006
WO    2006077466 A2    7/2006
(Continued)

*Primary Examiner* — Quynh-Nhu H Vu
(74) *Attorney, Agent, or Firm* — McDonnell Boehnen Hulbert & Berghoff LLP

(57) ABSTRACT

A drive assembly for a drug delivery device is disclosed. The drive assembly is connectable with a cartridge holder and comprises a housing, a piston rod, the piston rod being movable in a distal direction for drug delivery, and a guide nut, the guide nut being rotatable relative to the housing around an axis of the assembly and provided for guiding the piston rod. A locking means is provided which is enabled to take an engaged state in which the locking means is engaged with the guide nut in order to prevent rotation of the guide nut and to take a disengaged state in which the locking means is disengaged from the guide nut in order to allow rotation of the guide nut. Moreover, a coupling means is provided, the coupling means being rotatable relative to the housing around the axis of the assembly for interaction with the locking means in order to change between the engaged state and the disengaged state of the locking means.

15 Claims, 10 Drawing Sheets

(52) U.S. Cl.
CPC ............ *A61M 5/24* (2013.01); *A61M 5/31535* (2013.01); *A61M 5/31541* (2013.01); *A61M 5/31575* (2013.01); *A61M 2005/2407* (2013.01); *A61M 2005/2477* (2013.01); *A61M 2005/2488* (2013.01); *A61M 2205/581* (2013.01); *A61M 2205/582* (2013.01)

(56) References Cited

U.S. PATENT DOCUMENTS

| | | | | |
|---|---|---|---|---|
| 2003/0050609 A1* | 3/2003 | Sams | ............... | A61M 5/20 604/208 |
| 2006/0184117 A1* | 8/2006 | Knight | ............... | A61M 5/24 604/135 |
| 2009/0118669 A1* | 5/2009 | Bendek | ............... | A61M 5/2448 604/88 |
| 2009/0275914 A1* | 11/2009 | Harms et al. | ............... | 604/506 |
| 2010/0030158 A1* | 2/2010 | Christiansen | ............... | A61M 5/24 604/208 |
| 2011/0034881 A1* | 2/2011 | Bartha | ............... | A61M 5/24 604/211 |
| 2013/0030381 A1* | 1/2013 | Langley et al. | ............... | 604/224 |

FOREIGN PATENT DOCUMENTS

| | | |
|---|---|---|
| WO | 2008009656 A1 | 1/2008 |
| WO | 2008031235 A1 | 3/2008 |
| WO | 2009101005 A1 | 8/2009 |

* cited by examiner

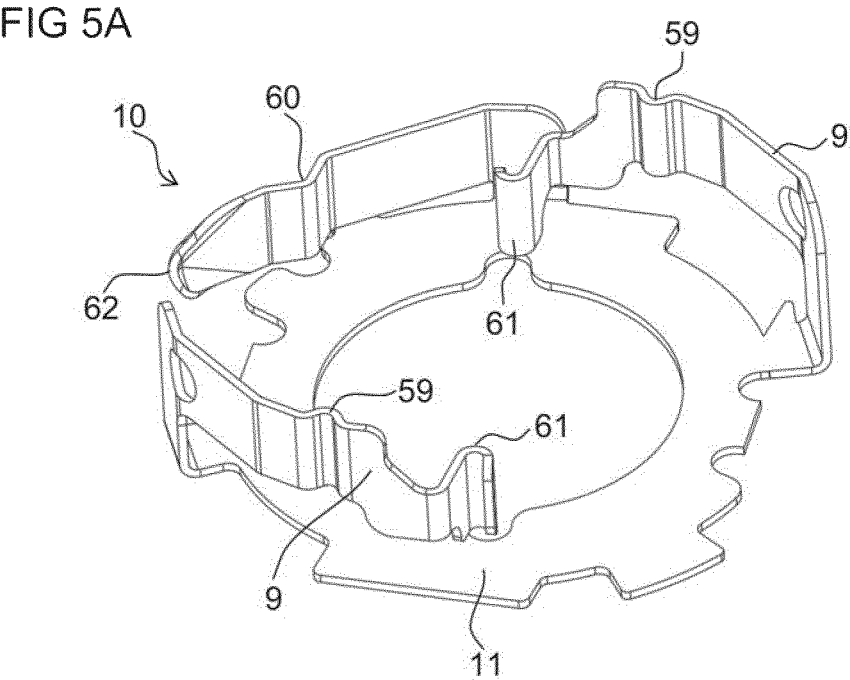

DRIVE ASSEMBLY FOR A DRUG DELIVERY DEVICE AND CORRESPONDING DRUG DELIVERY DEVICE

CROSS REFERENCE TO RELATED APPLICATIONS

The present application is a U.S. National Phase Application pursuant to 35 U.S.C. §371 of International Application No. PCT/EP2012/058181 filed May 4, 2012, which claims priority to European Patent Application No. 11165045.3 filed May 6, 2011. The entire disclosure contents of these applications are herewith incorporated by reference into the present application.

FIELD OF INVENTION

The present disclosure pertains to a drive assembly for a drug delivery device, the drive assembly being connectable with a cartridge holder. Moreover, the present disclosure pertains to a drug delivery device with a corresponding drive assembly and a cartridge holder.

BACKGROUND

Portable drug delivery devices are used for the administration of a medicament or drug, especially a medicinal fluid that is suitable for self-administration by a patient. A drug delivery device may comprise a syringe, an injection device, an injector or a pen-type injection device. In particular, a drug delivery device in the shape of a pen is useful, since it can be handled easily and kept available everywhere.

There exist different types of drug delivery devices. One type of a drug delivery device comprises a disposable device which may be disposed after having dispensed the medicament or after the medicament has been expired. Another type of a drug delivery device comprises a refillable drug delivery device which may be reusable many times. This kind of drug delivery device may comprise a drive assembly and a cartridge holder which is connectable to the drive assembly and which contains a cartridge, ampoule or vial containing a medicament or drug. Often, a needle assembly may be connected to a distal end of the cartridge holder for subcutaneous injection of the medicament. A dose of a drug or medicament is delivered by means of a drive mechanism of the drive assembly driving a piston rod or lead screw in a distal direction, the piston rod interacting with a piston within the cartridge for expelling the medicament out of the device. The drug delivery device may provide a dose-setting mechanism which allows setting the dose of the medicament that is to be dispensed.

In common devices, as disclosed in U.S. 2009/0275914 A1 for example, the piston rod is guided in the drive assembly by a guide nut, also called body nut or lead screw nut, which is coupled to the piston rod for moving the piston rod in distal direction during drug delivery. For this purpose, the guide nut is rotationally fixed with respect to the housing of the drive assembly in order to urge the piston rod into a predetermined, mostly helical movement.

In reusable drug delivery devices the situation may arise that the drug delivery device has to be reset. This means, the piston rod has to be moved in a proximal direction opposite to the distal direction back into the drive assembly such that a new cartridge contained within the cartridge holder may be assembled to the drive assembly in order to start a new cycle of drug delivery. During the reset operation of the piston rod, the guide nut may preferably be rotatable with respect to the housing in order to enable a quick and easy shifting of the piston rod back into the drive assembly. Thus, the guide nut has to fulfill double functionalities, wherein during drug delivery the guide nut has to be rotationally fixed and during a reset operation the guide nut has to be rotatable with respect to the housing. This is also disclosed in U.S. 2009/0275914 A1.

According to U.S. 2009/0275914 A1 the drug delivery device provide a locking means for releasable engagement with the guide nut in order to prevent rotational movement of the guide nut with respect to the housing during drug delivery and to allow rotation of the guide nut with respect to the housing during resetting of the device. The locking means may directly be operated by the cartridge holder when the cartridge holder is assembled to the drive assembly.

SUMMARY

It is an object of the present disclosure to present a new drive assembly for a drug delivery device and a new drug delivery device providing for a better and safe handling.

This object is achieved by a drive assembly and a drug delivery device according to claims. Further objects are achieved by variants and alternative or preferred embodiments according to the dependent claims.

The drive assembly comprises a housing or body and a lead screw or piston rod, the piston rod being movable in a distal direction for drug delivery. Moreover, the drive assembly provides a lead screw nut or guide nut being rotatable relative to the housing around an axis of the assembly and being provided for guiding the piston rod. A locking means is provided, the locking means being enabled to take an engaged state in which the locking means is engaged with the guide nut in order to prevent rotation of the guide nut. Moreover, the locking means is enabled to take a disengaged state in which the locking means is disengaged from the guide nut in order to allow rotation of the guide nut. Furthermore, the drive assembly provides a coupling means, the coupling means being rotatable relative to the housing around the axis of the assembly for interaction with the locking means in order to change between the engaged state and the disengaged state of the locking means.

The disclosed drive assembly provides, besides a guide nut and a locking means, a coupling means that may interact with the locking means in such a way as to enable switching of the locking means between the two states. Thus, the coupling means may provide better coupling or decoupling of the locking means with or from the guide nut. Erroneous engagement of the locking means with the guide nut due to an unstable mounting position of the cartridge holder may, therefore, be prevented. This may aid a user in better handling the device.

The guide nut can be a single component or can be composed of two or more parts. It can especially be formed to guide the movement of the piston rod, providing for example a screw thread for coupling the piston rod. The guide nut may be provided to engage with another component of the drive assembly by means of a friction or by means of a structured surface on the guide nut, which may comprise one or more notches, teeth, grooves, spikes or similar structure elements.

The locking means can be any component that is suitable to engage with the guide nut in such a way as to prevent rotation of the guide nut with respect to the housing of the drive assembly. The locking means can be designed according to the requirements of individual embodiments. Hence, the locking means can comprise a cantilever- or leaf spring-structure with a hook, a pawl or an edge for engagement with the structure elements of the guide nut as explained above. Moreover, the locking means can be resilient or resiliently mounted with respect to the guide nut and/or with respect to the coupling means.

The locking means may take two states. A first state represents an engaged state in which the locking means is engaged with the guide nut in order to prevent rotation of the guide nut. This state is preferably taken during drug delivery. A second state represents a disengaged state in which the locking means is disengaged from the guide nut in order to allow rotation of the guide nut. This state is preferably taken during a reset operation as explained above.

The coupling means can be any component that is suitable to effect the engagement of the locking means with the guide nut. The coupling means can be formed of only one part or assembled from two or more parts. Moreover, it can be designed to engage or couple with the locking means in any mechanical way that is suitable to change the state of the locking means, i.e. the relative position of the locking means with respect to the guide nut. In particular, the coupling means can be rotated in such a way that an engagement of the locking means with the guide nut is allowed or prevented. In case, engagement of the locking means with the guide nut is prevented, the locking means is released from the guide nut and a rotational movement of the guide nut is allowed which can especially be provided for a reset operation. The coupling means thus may interact with the locking means in order to switch the state of the locking means between the engaged state and the disengaged state.

In a preferred embodiment the coupling means is rotatable between a first position and a second position, wherein in the first position the coupling means prevents engagement of the locking means with the guide nut and wherein in the second position the coupling means allows engagement of the locking means with the guide nut. Thus, the first position of the coupling means represents the engaged state of the locking means, whereby the second position of the coupling means represents the disengaged state of the locking means. Preferably, the coupling means rests either in the first position or in the second position without resting in intermediate positions between the first and second position. That means, the first and second positions describe discrete states of the coupling means, wherein in the first position the locking means is definitely engaged with the guide nut and wherein in the second position the locking means is definitely disengaged from the guide nut such that erroneous behavior of the drive assembly may not occur or at least may be reduced.

As described above, the locking means is preferably engaged with the guide nut for moving the piston rod in the distal direction during drug delivery. That means, the guide nut is rotationally fixed with respect to the housing and may urge the piston rod into a predetermined movement in distal direction. Preferably, the locking means is disengaged from the guide nut for enabling a reset operation, thereby moving the piston rod in a proximal direction opposite to the distal direction, the guide nut being enabled to rotate relative to the housing. When the locking means is disengaged from the guide nut, the guide nut may be rotated such that the piston rod may be axially shifted in proximal direction, in order to allow simple and quick resetting of the drive assembly.

Preferably, the locking means is rotationally fixed with respect to the housing. Independent of any state or position the locking means remains rotationally fixed to the housing. Hence, a change of position of the locking means caused by a rotation of the locking means with respect to the housing may not occur. Also, any rotational movement of the guide nut with respect to the housing is therefore prevented when the guide nut is coupled to the locking means, in particular during drug delivery, wherein the guide nut is expected to remain rotationally fixed to the housing.

According to one embodiment the coupling means provides one or more first fastening members for engagement with one or more corresponding second fastening members of a cartridge holder, the coupling means being rotatable by actuation of the first fastening members. The first fastening members of the coupling means are designed such that they may interact with at least a part of a cartridge holder when the cartridge holder is assembled to the drive assembly. That means, the first fastening members are directed in distal direction towards an opening of the housing of the drive assembly such that second fastening members of a cartridge holder may couple to and interact with the first fastening members.

It is conceivable that the coupling means is rotated via the first fastening members caused by a rotational mounting movement of the cartridge holder upon engagement of the first and second fastening members when the cartridge holder is mounted on a distal end of the assembly. That means, switching between the engaged state and the disengaged state of the locking means via the coupling means may be effected by a rotational mounting movement during assembly of a cartridge holder. Thus, engagement between the locking means and the guide nut may be operated by mounting the cartridge holder to the drive assembly. According to this, the coupling means may act as an intermediary between the cartridge holder and the assembly of the locking means and the guide nut.

According to one embodiment, the guide nut is at least partially encompassed by the coupling means and the locking means. In particular, the locking means is designed to perform radial movement during switching between the engaged state and the disengaged state. A rotational movement of the coupling means may effect the radial movement of the locking means. Thus, the locking means may interact with the guide nut when the locking means moves in radial direction towards the axis of the assembly caused by rotational movement of the coupling means.

Preferably, the coupling means is designed as a ring-shaped member providing one or more radial recesses. The locking means may be circumferentially arranged on at least a part of the exterior of the coupling means. According to this arrangement the locking means may pass the radial recesses of the coupling means in order to engage with the guide nut. Preferably, the locking means may be a resilient or resiliently mounted member that is tensioned in radial direction towards the axis of the assembly. This has the effect that during the disengaged state of the locking means the coupling means holds the locking means out of engagement with the guide nut, whereby for switching into the engaged state of the locking means the coupling means releases the locking means such that the locking means may be urged to pass the recesses of the coupling means caused by spring forces and may engage with the guide nut.

It is also conceivable to arrange the coupling means circumferentially on at least a part of the exterior of the locking means. In this case, the locking means may be resilient or resiliently mounted and tensioned in radial direction away from the axis of the assembly. Contrary to the above-explained embodiment, during the engaged state the coupling means urges the locking means into engagement with the guide nut against a spring force, whereby for switching in the disengaged state the coupling means releases the locking means out of engagement with the guide nut, the locking means passing the radial recesses of the coupling means in radial direction away from the axis of the drive assembly caused by spring forces, thereby disengaging from the guide nut.

According to one embodiment, a part of the interior of the coupling means near the one or more radial recesses is designed as a ramp providing a transition from a narrowed diameter to a broader diameter of the interior of the coupling means towards the one or more radial recesses. The ramp provides a kind of angled cut-out which smoothly receives at least a part of the locking means and prevents the locking means to scratch with a sharp edge on the wall of the coupling means and to damage the coupling means. In particular, torsional moments may occur on the guide nut during interaction with a piston rod guided by the guide nut during drug delivery or while trying to deliver a drug when the needle is blocked, which means an increased application of force. These torsional moments may urge the locking means into radial movement away from the axis of the assembly. This movement does not lead to a disengagement of the locking means from the guide nut, but provokes heavy contact forces between the locking means and the coupling means, the effect of which is notably attenuated due to the above explained ramp-shape of the coupling means near the radial recesses of the coupling means. Additionally or alternatively, the ramp may be shaped such that when the locking means is urged radially outwards, a contact between the locking means and the coupling means is established in an area different from the sharp edge of the locking means. Thereby, a damage of the coupling means by a contact with the sharp edge of the locking means can be prevented.

According to one embodiment, the coupling means comprises one or more retaining means for retaining the coupling means within the housing and for preventing axial movement of the coupling means with respect to the housing. This means, the coupling means are exclusively rotatable with respect to the housing, thereby actuating the locking means in order to switch the locking means between the engaged state (engagement with the guide nut) and the disengaged state (disengagement from the guide nut).

According to another embodiment, the locking means comprise two members arranged on opposite sides of a carrier, wherein the carrier is rotationally fixed with respect to the housing. The members may be designed as two arms or cantilevers which are arranged on opposite sides of the carrier. The locking means may be designed such that one end of the locking means is fixed to the carrier and the other end of the locking means is free. At a respective free end, a locking means may provide an edge, pawl or hook for engagement with corresponding notches or interspaces of a guide nut. Preferably, as explained above, the locking means are resiliently mounted on the carrier. Thus, the locking means may be pivoted on their free ends with the hooks thereon towards the centre of the carrier. Thus, the locking means may perform a radial movement for engagement with the guide nut.

According to one embodiment, the free end of the cantilever provides a sinusoidal shape with at least two reverse loops, wherein a first loop is molded towards the axis of the assembly and forms the edge, pawl or hook and wherein a second loop is molded away from the axis of the assembly and finishes in the free end of the cantilever, the second loop being designed to at least partially contact with a part of the coupling means in the engaged state of the locking means. This embodiment may also provide for a save engagement and contact between the locking means and the coupling means without the risk of any damage of the coupling means due to scratching of one end of the locking means on the coupling means during torsional moments as explained above.

In further embodiments of the drive assembly, the guide nut comprises a screw thread for coupling the piston rod and enabling a helical movement of the piston rod relative to the guide nut. The helical movement thereby comprises a concurrent axial and rotational movement of the piston rod. That means the piston rod is threaded through the guide nut during drug delivery according to a predetermined, e.g. helical movement.

The drive assembly may further comprise a drive sleeve for driving the piston rod, wherein the drive sleeve is arranged within the housing and is coupled with the piston rod by means of a further screw thread. Preferably the screw thread of the guide nut and the further screw thread have opposite senses of rotation. A clutch may be provided within the drive assembly allowing the drive sleeve to be rotationally locked with respect to the housing in a releasable manner. This may affect a shift of the drive sleeve relative to the housing along the axis, the shift of the drive sleeve being converted into a helical movement of a piston rod relative to the housing when the drive sleeve is rotationally locked relative to the housing and the locking means is engaged with the guide nut. Thus, the piston rod may be urged into helical movement for drug delivery.

The disclosure further relates to a drug delivery device comprising a drive assembly as explained above and a cartridge holder. The cartridge holder may be releasably mounted on a distal end of the assembly and may be engaged with the coupling means, the coupling means interacting with the locking means such that the locking means is in the engaged state. The cartridge holder may comprise a cartridge containing a medicament or drug to be dispensed.

The drug delivery device can generally be a disposable or reusable device designed to dispense a dose of a drug. The device may be designed to be operated manually or electrically and may comprise a mechanism for setting a dose. The device may be further designed to monitor physiological properties like blood glucose levels, for example. Furthermore, said device may comprise a needle or may be needle-free.

The term "medicament" or "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(0)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

The features as explained above as well as other features will become apparent from the following description of drawings. Same elements are related with same reference numerals.

FIG. 5A shows a perspective view of a first embodiment of a mounting device providing locking means of the drive assembly.

DETAILED DESCRIPTION

Figure 1:
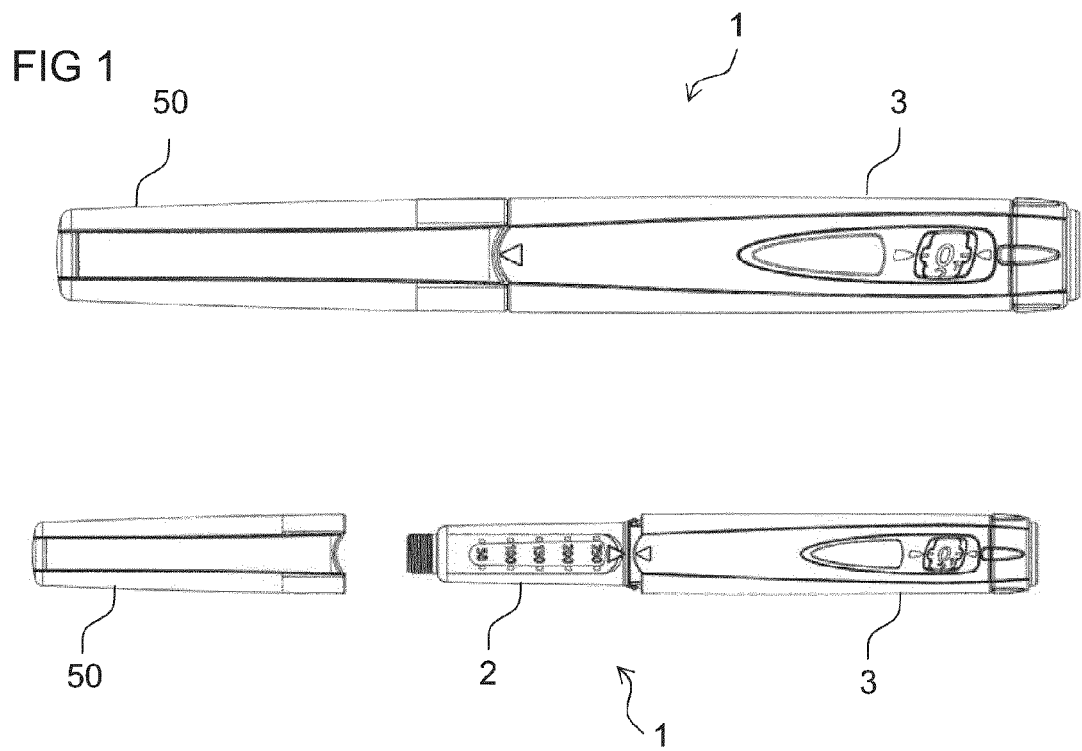
FIG. 1 shows an embodiment of a drug delivery device in a capped and uncapped state.

FIG. 1 shows an embodiment of a drug delivery device 1. The drug delivery device 1 according to this embodiment is a pen-shaped injection device providing a housing 3 of a drive assembly. A protective cap 50 may be slid over a cartridge holder 2 which is mounted on a distal end of the housing 3 of the drive assembly. The protective cap 50 may cover at least a part of the cartridge holder 2 in order to cover and protect the cartridge holder 2 from environmental influences. The drug delivery device 1 may be a so-called reusable device, wherein the cartridge holder 2 may be releasably secured to the housing 3 and wherein the drive assembly within the housing 3 may be reused many times.

Figure 2:
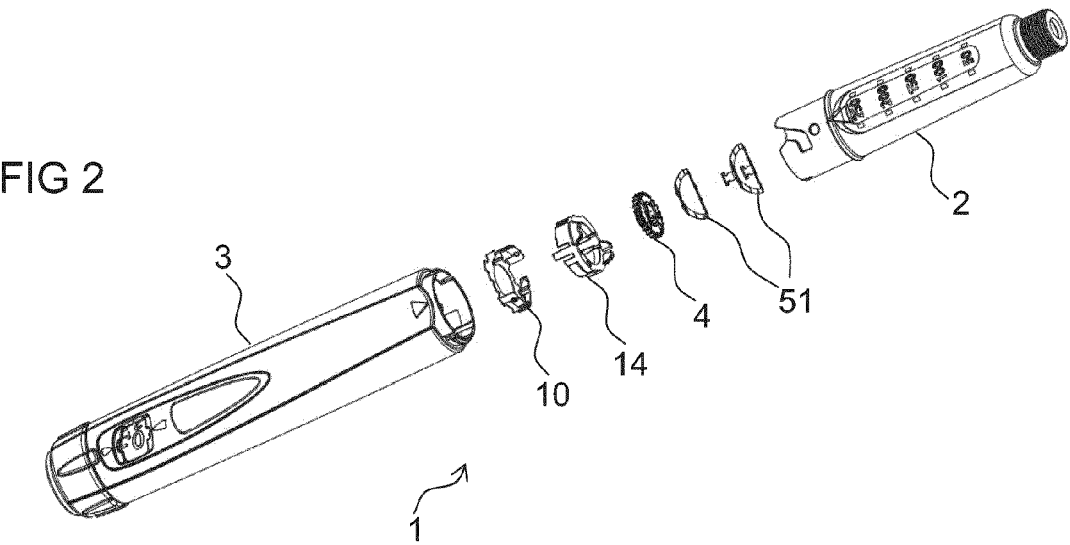
FIG. 2 shows a perspective view of several parts of the drug delivery device according to FIG. 1.

FIG. 2 shows a perspective view of several parts of the drug delivery device 1 according to FIG. 1. In particular, the drug delivery device 1 provides the housing 3 and the cartridge holder 2 as explained above. Moreover, a mounting device 10 and coupling means 14 are provided which, according to this embodiment, are hollow or ring-shaped members that may encompass a guide nut 4 when assembled within the housing 3.

Moreover, two bias springs 51 are provided in order to provide a spring force against a cartridge (not shown in detail) contained within the cartridge holder 2 in order to hold the cartridge in a predetermined position at a distal end of the cartridge holder 2. In particular, the coupling means 14, the guide nut 4, and the mounting device 10 are described in the following.

Figure 3:
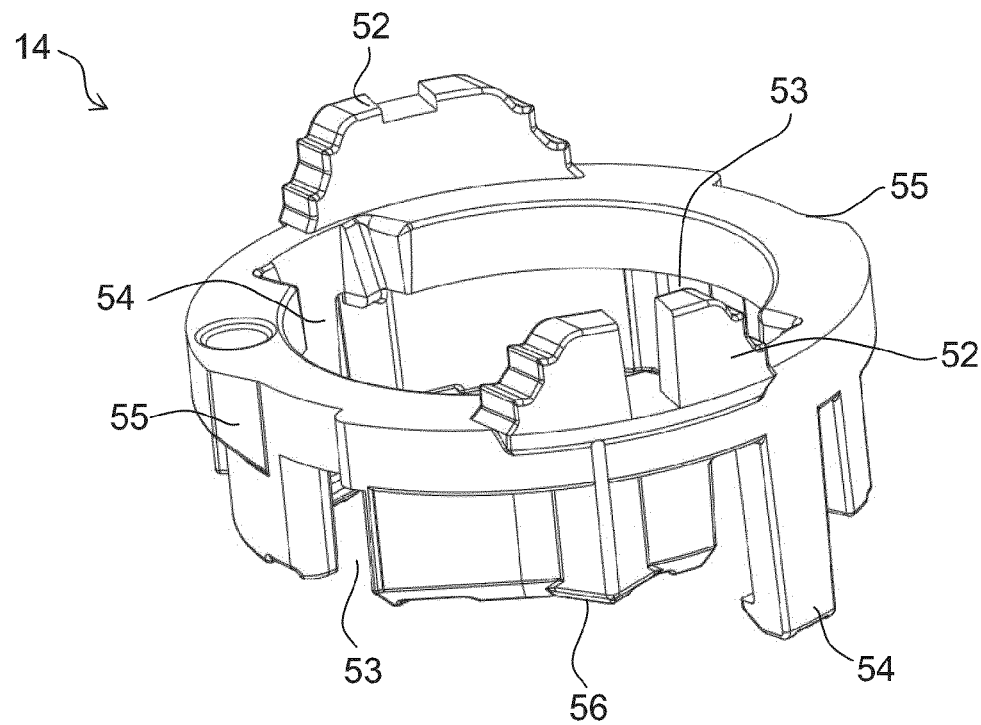
FIG. 3 shows a perspective view of a coupling means of a drive assembly of the drug delivery device.

FIG. 3 shows a perspective view of the coupling means 14 according to FIG. 2. The coupling means 14 is a ring-shaped member which may be assembled within the housing 3 of the drive assembly such that it is rotatable with respect to the axis of the drive assembly. Hence, the coupling means 14 may act as a so called turning ring. Moreover, the coupling means 14 provides retaining means 54 that are arranged on opposite sides of the ring-shaped body of the coupling means 14 in order to retain the coupling means 14 within the housing and to prevent axial movement of the coupling means 14 within the housing 3.

The coupling means 14 according to the embodiment of FIG. 3 provides radial recesses 53 on opposite sides of its main body. Thus, the coupling means 14 is a hollow member, not only in axial direction, but also in radial direction. The recesses 53 have the effect that the locking means 61 of a mounting device 10 (as shown in greater detail in FIGS. 5A and 6A) may pass the radial recesses 53 towards the center of the coupling means 14 in order to engage with a guide nut 4 as explained below.

Moreover, the coupling means provides a ramp-shaped exterior surface providing two ramps 55 arranged at opposite sides of the exterior of the coupling means 14. The ramps 55 are angled ramps providing a transition from a broader diameter to a narrowed diameter of the exterior of the coupling means 14. The ramps 55 are arranged substantially at the positions of the corresponding radial recesses 53. The ramps 55 are designed in order to enable a locking means 61 of a mounting device 10 to slide along the exterior surface of the coupling means 14 from the broader part to the narrowed part and to perform a radial movement towards the center of the coupling means 14 when reaching the narrowed diameter of the coupling means 14. Interaction between the coupling means 14 and the locking means 61 of the mounting device 10 will be explained in greater detail with regard to FIG. 6A.

Moreover, the coupling means 14 provides a protrusion 56 that may interact with a corresponding member of the mounting device 10 in order to hold and secure the coupling means 14, either in a first or in a second position, wherein the coupling means 14 may be rotated between the first and the second position. The protrusion 56 may aid the coupling means 14 in resting in either of the both positions, not resting in but only traversing positions between the first and the second position. The protrusion 56 is wedge-shaped wherein the coupling means 14 may rest in the first position, the corresponding element of the mounting device being arranged at one side of the wedge-shaped protrusion 56, and wherein the coupling means 14 may rest in the second position, the corresponding element of the mounting device being arranged at the other side of the wedge-shaped protrusion 56. This may aid in defining two discrete positions of the coupling means 14 with respect to the housing. See also general explanations with regard to FIGS. 5A, 5B, and 5C.

Furthermore, the coupling means 14 provides first fastening members 52 arranged on opposite sides at the top of the ring-shaped body of the coupling means 14. The first fastening members 52 are provided for interaction and engagement with corresponding second fastening members 63 of a cartridge holder 2 (see also FIG. 7). The coupling means 14 may be operated e.g. rotated, via the first fastening members 52. According to this embodiment, the coupling means 14 may be rotated during a mounting movement of a cartridge holder 2 when assembled to the drive assembly as explained with regard to FIG. 7.

Figure 4:
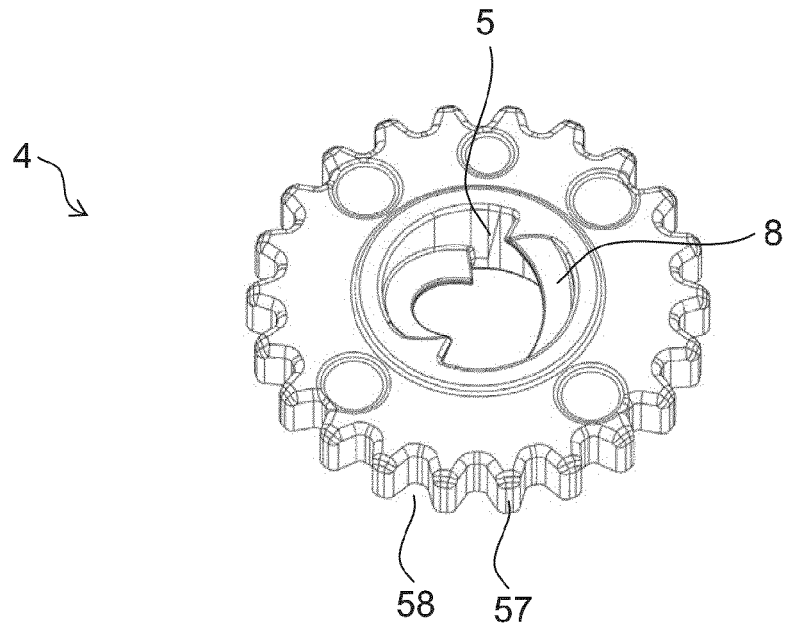
FIG. 4 shows a perspective view of a guide nut of the drive assembly of the drug delivery device.

FIG. 4 shows a perspective view of a guide nut 4 providing a centered hole 5. Within the centered hole 5 a screw thread 8 is designed for coupling a piston rod of the drive assembly in order to urge the piston rod in a predetermined helical movement as explained in greater detail with regard to FIG. 8. Moreover, according to this embodiment, the guide nut 4 is designed as a toothed wheel providing teeth 57 and notches 58 on the exterior circumference of the guide nut 4. The teeth 57 and notches 58 may be adapted to individual embodiments of the guide nut 4. Thus, the teeth 57 may be designed as spikes, whereby the notches 58 may be designed as interspaces between the teeth 57 or spikes. The guide nut 4 may be rotationally arranged within the housing 3 of the drive assembly. In one state of the drive assembly, preferably during drug delivery, the guide nut 4 may be rotationally fixed by locking means 9 of a mounting device 10 as explained with regard to FIGS. 6A, 6C, and 6E. In another state of the drive assembly, preferably during a resetting operation, the guide nut may be rotatable with respect to the housing 3 of the drive assembly as explained with regard to FIGS. 6A, 6B and 6D. The coupling means 14, according to FIG. 3 (and according to other embodiments as explained with regard to FIGS. 6B through 6E), may act as an actuation means in order to enable a switching between an engaged state and a disengaged state of the locking means 9 of the mounting device 10 with respect to the guide nut 4.

Figure 5B:
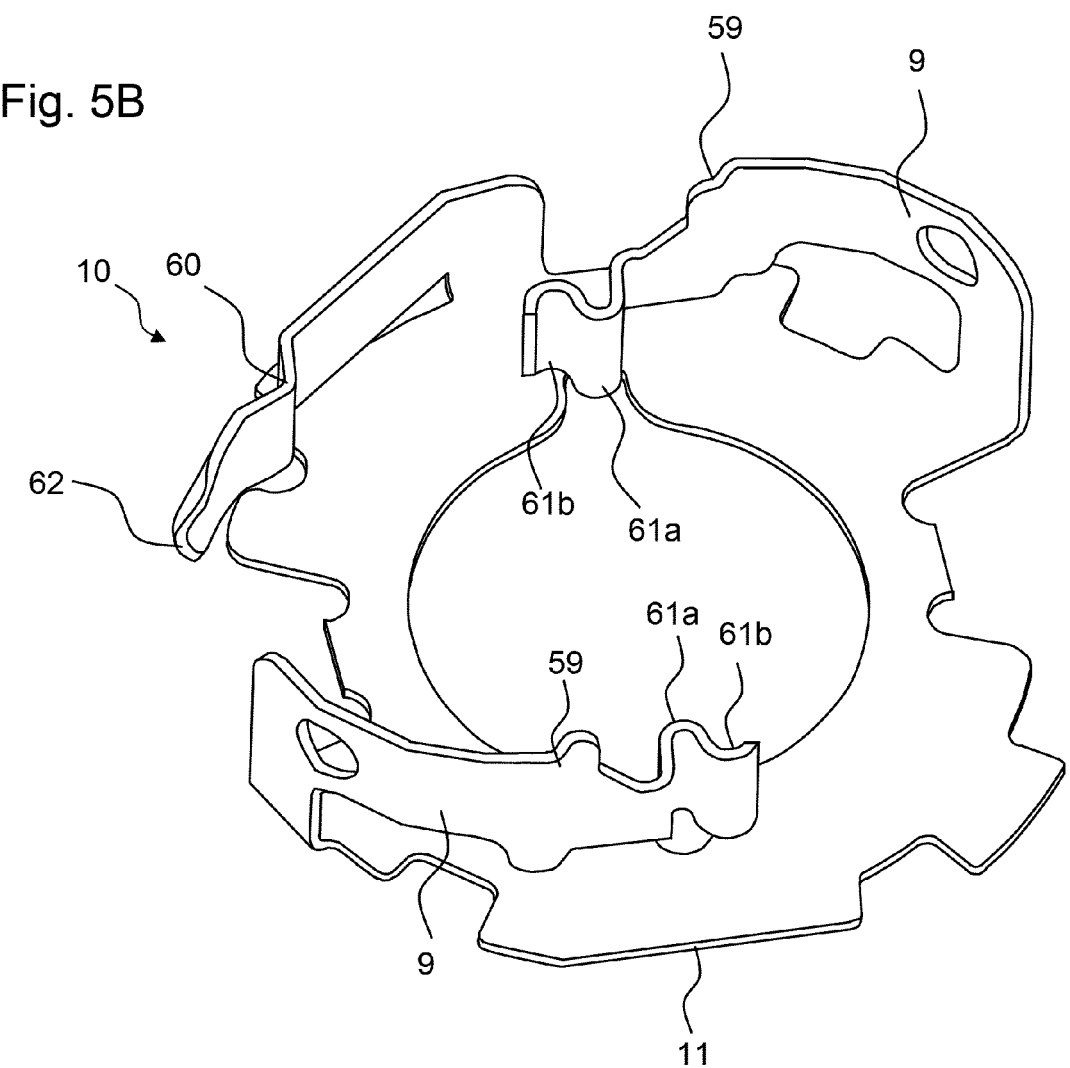
FIG. 5B shows a perspective view of a second embodiment of a mounting device providing locking means of the drive assembly.
Figure 5C:
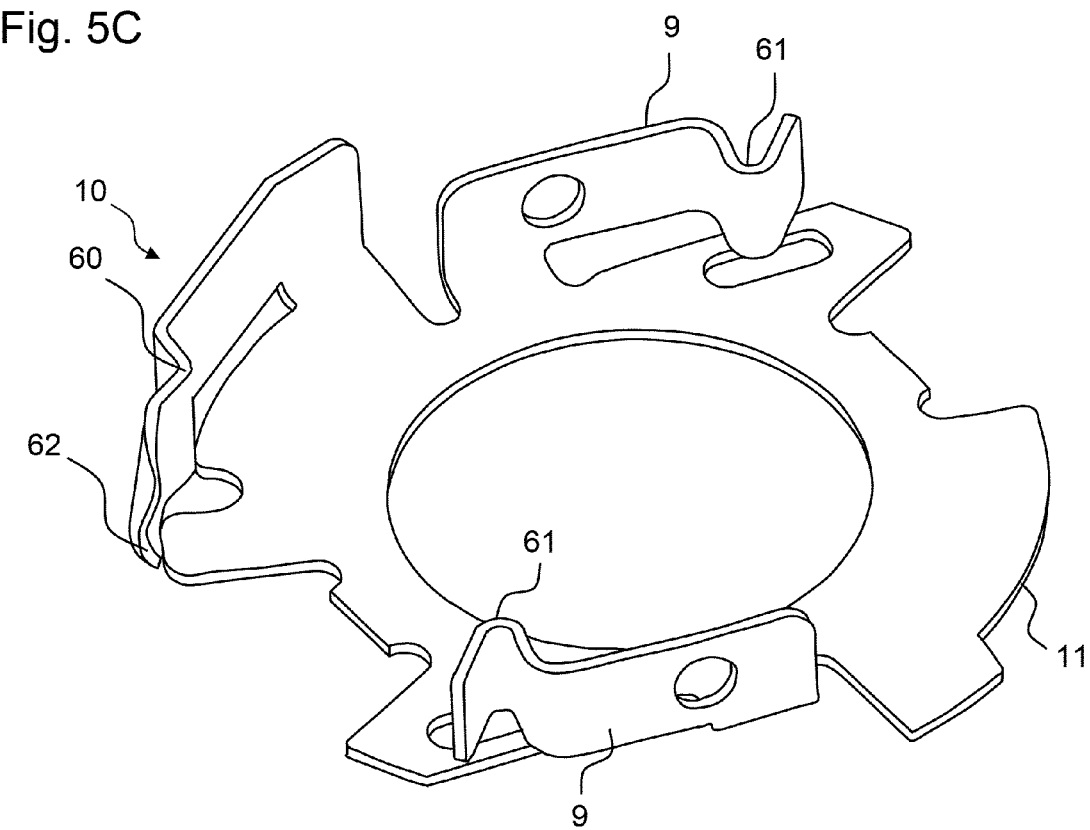
FIG. 5C shows a perspective view of a third embodiment of a mounting device providing locking means of the drive assembly.

FIGS. 5A through 5C show different embodiments of a mounting device 10 providing a ring-shaped carrier 11 on which locking means 9 are formed. In detail the locking means 9 comprise two arms or cantilevers which are arranged on opposite sides of the carrier 11. With one end, the locking means 9 are fixed to the carrier 11 and with the other end the locking means 9 are free. At a respective free end, a locking means 9 provides an edge or a hook 61 for engagement with corresponding notches 58 or interspaces of a guide nut 4 according to FIG. 4. The locking means 9 are resiliently mounted on the carrier 11. Thus, the locking means 9 may be pivoted on their free ends with the hooks 61 thereon towards the centre of the carrier 11. Thus, the locking means 9 may perform a radial movement.

Furthermore, the mounting device 10 provides a retaining means 62 being formed as another cantilever-structure with a fixed end on the carrier 11 and a free end pointing substantially in a tangential direction with respect to the ring-shaped carrier 11. The retaining means 62 provides a protrusion 60 for interaction with the wedge-shaped protrusion 56 of the coupling means 14 according to FIGS. 3, 6B, and 6C in order to hold the coupling means 14 in either a first position or in a second position, the protrusion 60 sliding along the wedge-shaped protrusion 56 of the coupling means 14 with the effect on the coupling means as explained with regard to FIG. 3. Thus, the mounting device may act as a so called multi-spring element providing resilient locking means 9 as well as resilient retaining means 62.

According to a first embodiment of the mounting device 10 as shown in FIG. 5A, the locking means 9 provide protrusions 59 which are molded on the cantilever-formed locking means 9 and which are directed towards the centre of the carrier 11. The protrusions 59 are designed for sliding along the ramps 55 on the exterior of the coupling means 14 (see FIG. 3). For further details see FIG. 6A.

A second embodiment of the mounting device 10 as shown in FIG. 5B differs from the first embodiment as shown in FIG. 5A in that the free ends of the cantilever-formed locking means 9 are bent such that an edge is provided forming protrusions 59 for engagement with a part of the coupling means 14 in order to actuate the locking means 9. Moreover, the respective free ends of the cantilever-formed locking means 9 provide a sinusoidal shape with at least two reverse loops 61a and 61b, wherein a first loop 61a is molded towards the axis of the assembly and forms the hook, edge or pawl 61 for engagement with respective teeth 57 of the guide nut 4 (see FIG. 4) and wherein a second loop 61b is molded away from the axis of the assembly and finishes in the free end of the cantilever. The second loop 61b is designed to at least partially contact with a part of the coupling means 14 in the engaged state of the locking means 9, i.e. when the locking means 9 are actuated by the coupling means 14 and engage with the guide nut 4. In particular, in the engaged state, the second loop 61b may be tangentially arranged with respect to a corresponding part of the coupling means 14, thereby providing for a smooth contact with the coupling means 14. This embodiment may provide for a save engagement and contact between the locking means 9 and the coupling means 14 without the risk of any damage of the coupling means 14 due to scratching of a sharp edge of a free end of the locking means 9 on the coupling means 14 during torsional moments.

In the first and second embodiments of the mounting device 10, the resilient locking means 9 may be tensioned in radial direction towards the axis of the carrier 11 such that spring forces may urge the locking means 9 towards the axis of the assembly for engagement with teeth 57 of the guide nut 4 (see FIG. 4). That means, the coupling means 14 may engage with the locking means 9 in order to urge the locking means 9 in radial direction away from the axis and out of engagement with the guide nut 4 opposite to the spring forces of the tensioned locking means 9. In the contrary, when the locking means 9 are to be brought into the engaged state, the coupling means 14 may release the locking means 9 such that the locking means 9 are urged in radial direction towards the axis of the assembly due to the radial spring forces of the locking means 9.

A third embodiment of the mounting device 10 as shown in FIG. 5C differs from the first and second embodiments as shown in FIGS. 5A and 5B in that the locking means 9 with its cantilevers are arranged such that the interaction of the coupling means 14 and the locking means 9 works in opposite manner according to the principle of the embodiments of FIGS. 5A and 5B. That means, according to the embodiment of FIG. 5C, the resilient locking means 9 are tensioned in radial direction away from the axis of the carrier 11 such that spring forces may urge the locking means 9 away from the axis of the assembly for disengagement from teeth 57 of the guide nut 4 (see FIG. 4). That means, the coupling means 14 may engage with the locking means 9 in order to urge the locking means 9 in radial direction towards the axis and into engagement with the guide nut 4 opposite to the spring forces of the tensioned locking means 9. In the contrary, when the locking means 9 are to be brought in the disengaged state, the coupling means 14 may release the locking means 9 such that the locking means 9 are urged in radial direction away from the axis of the assembly due to the spring forces of the locking means 9. For further explanation in this regard, see FIGS. 6B and 6C and their respective description below.

Figure 6A:
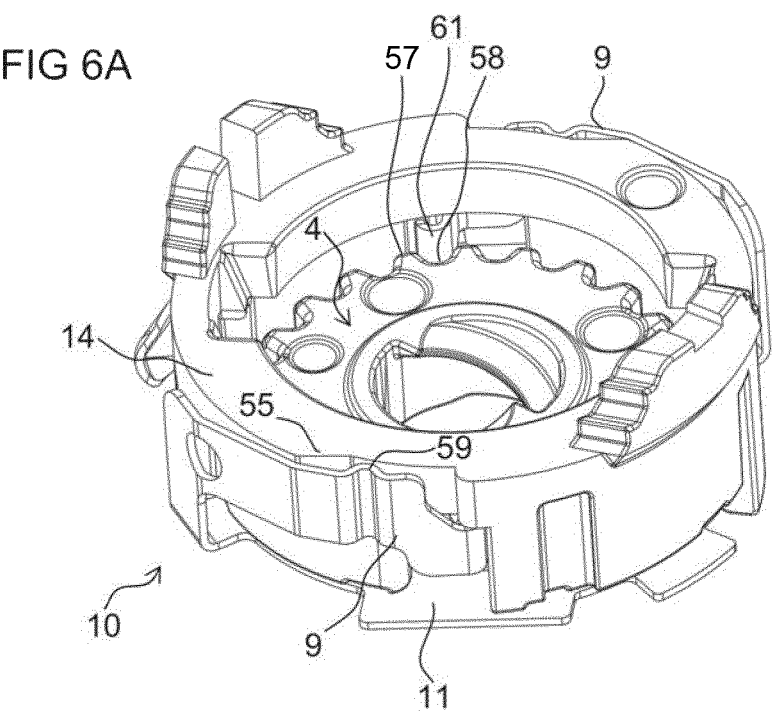
FIG. 6A shows a perspective view of an assembled coupling means, guide nut and mounting device according to FIGS. 3 through 5A.

FIG. 6A shows an assembly of the coupling means 14, the mounting device 10 and the guide nut 4 according to FIGS. 3 through 5A. The guide nut 4 is encompassed by the coupling means 14 and the mounting device 10. The coupling means 14 provides a ledge on the inner circumference of the ring-shaped body in order to hold the guide nut 4 within the coupling means 14 and to prevent upward movement of the guide nut 4 out of the ring-shaped body of the coupling means. Moreover, the guide nut 4 may additionally be hold by a part of the carrier 11 of the mounting device 10 or by a part of the housing 3, e.g. a web-shaped part within the housing 3, in order to prevent downward movement of the guide nut 4. This means, the guide nut 4 is securely embedded between the coupling means 14 and the carrier 11 of the mounting device 10 or a part of the housing 3.

Furthermore, the locking means 9 of the mounting device 10 are circumferentially arranged on at least a part of the exterior of the coupling means 14. Thereby, the protrusions 59 (see also FIG. 5A) of the cantilever-formed locking means 9 are directed towards the exterior surface of the coupling means 14. This may have the effect that the locking means 9 may slide via the protrusions 59 along the ramps 55 on the exterior of the coupling means 14.

FIG. 6A shows a position of the coupling means 14 representing an engaged state of the locking means 9. The locking means 9 have passed with their free ends the radial recesses 53 of the coupling means 14 as explained in the context of FIG. 3. This is enabled due to the fact that the protrusions 59 are lying on the narrowed part of the diameter of the coupling means 14.

In the depicted position, the locking means 9 engage via their hooks 61 with the guide nut 4. In particular, the hooks 61 rest between the teeth 57 in respective notches 58. Moreover, in this position the hooks 61 engage behind a corresponding edge of the radial recesses of the coupling means 14. This has the effect that a radial movement of the hooks 61 out of engagement with the teeth 57 and away from the guide nut 4 due to torsional moments is prevented in order to enable a secure engagement between the locking means 9 and the guide nut 4. In particular, torsional moments may occur during interaction with the guide nut 4 and a piston rod guided by the guide nut 4 during drug delivery or while trying to deliver a drug but having a bent needle, which means an increased application of force.

In the position as depicted in FIG. 6A rotational movement of the guide nut 4 with respect to the mounting device 10 is prevented. In other words, the guide nut is rotationally fixed with respect to the mounting device 10. Since the mounting device 10 may be arranged within the housing 3 of the drive assembly in a rotationally fixed manner, the guide nut 4 may also be rotationally fixed with respect to the housing 3 of the drive assembly. In this position which preferably may be taken during drug delivery, the guide nut 4 may urge a piston rod to be moved in a predetermined movement, i.e. a helical movement, thereby being threaded through the inner screw thread 8 of the guide nut 4 (see FIG. 4).

In case, the coupling means 14 according to FIG. 6A is rotated counter clockwise, the protrusions 59 of the locking means 9 will slide along the angled ramp 55 of the coupling means 14 from the narrowed part to the broader part of the diameter of the coupling means 14. Hence, the locking means 9, i.e. the hooks 61, will be urged out of engagement with the notches 58 of the guide nut 4, the locking means 9 pivoting in radial direction away from the centre of the assembly. Thus, by rotating the coupling means 14, the locking means 9 may be released out of engagement with the guide nut 4. This may allow the guide nut 4 to rotate with respect to the mounting device 10. When the assembly is arranged within the housing 3 of the device, the guide nut 4 is allowed to rotate with respect to the housing 3 of the drive assembly such that a reset operation of the piston rod being coupled with the guide nut 4 may be started. This means, the piston rod may be shifted in proximal direction, the guide nut 4 being enabled to rotate with respect to the housing 3.

Figure 6B:
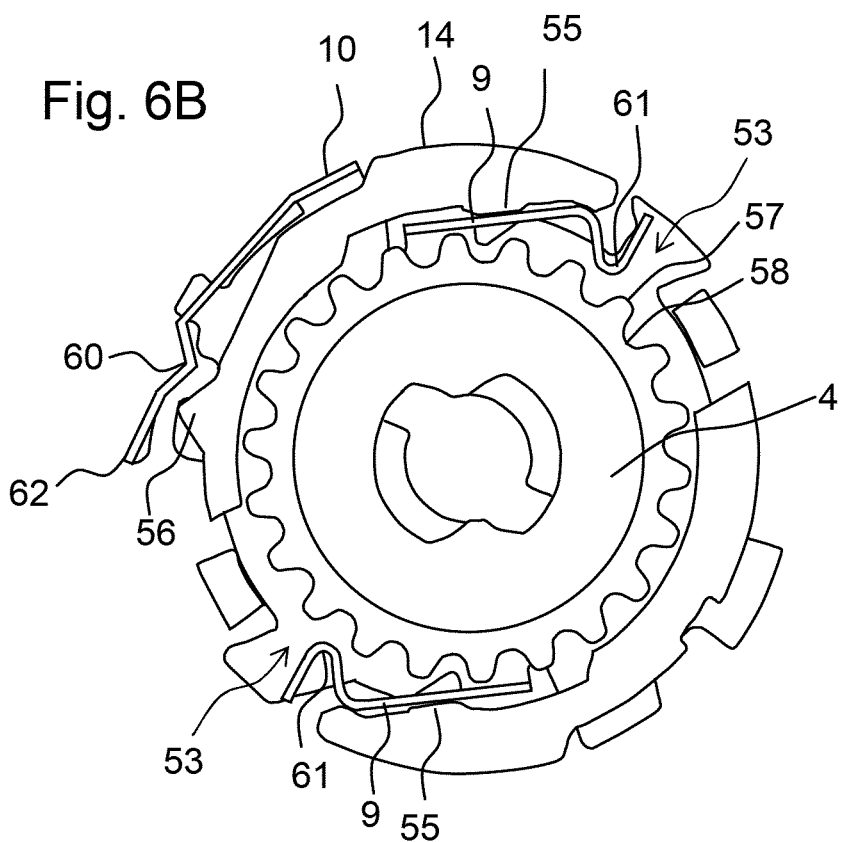
FIG. 6B shows a top view of an assembled coupling means, guide nut and mounting device according to a second embodiment in the disengaged state.
Figure 6C:
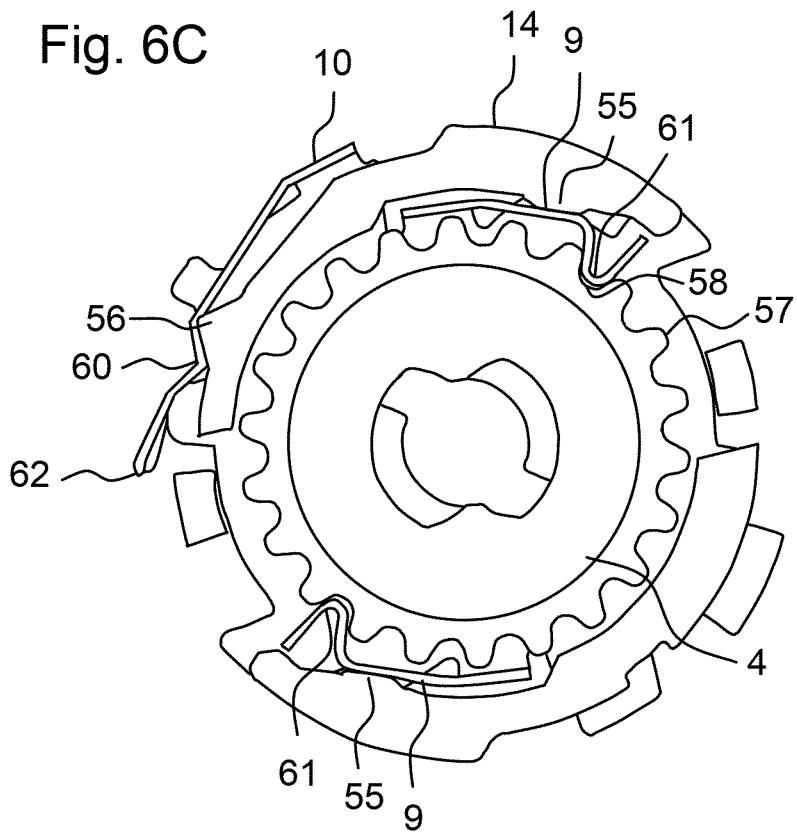
FIG. 6C shows a top view of an assembled coupling means, guide nut and mounting device according to the embodiment of FIG. 6B in the engaged state.

The FIGS. 6B and 6C respectively show a top view of an assembled coupling means 14, guide nut 4 and mounting device 10 according to a second embodiment in the disengaged state and the engaged state as well. In particular, the mounting device 10 is designed according to its embodiment shown in FIG. 5C. In contrast to the assembly according to FIG. 6A, in the assembly of FIGS. 6B and 6C, the coupling means 14 is circumferentially arranged on at least a part of the exterior of the locking means 9 of the mounting device 10. The locking means 9, according to this embodiment may be resilient and may be tensioned in radial direction away from the axis of the assembly (in contrast to the embodiment of FIG. 6A, wherein the locking means 9 may be tensioned in radial direction towards the axis of the assembly).

FIG. 6B illustrates the disengaged state of the assembly. The locking means 9, i.e. the hooks 61, are located at least partially in recesses 53 of the coupling means 14 and, therefore, are out of engagement with the notches 58 and the teeth 57 respectively of the guide nut 4. This state allows the guide nut 4 to rotate with respect to the mounting device 10. When the assembly is arranged within the housing 3 of the device, the guide nut 4 is allowed to rotate with respect to the housing 3 of the drive assembly such that a reset operation of the piston rod being coupled with the guide nut 4 may be started. This means, the piston rod may be shifted in proximal direction, the guide nut 4 being enabled to rotate with respect to the housing 3.

Moreover, as illustrated in FIG. 6B, the protrusion 56 of the coupling means 14 is arranged on one side of the protrusion 60 of the retaining means 62 of the mounting device 10 defining the disengaged state as a discrete state (see also the general explanation in context of FIGS. 5A through 5C above).

FIG. 6C illustrates the engaged state of the assembly. Starting from the position of the coupling means 14 according to FIG. 6B, the engaged state may be taken by rotating the coupling means 14 clockwise, the angled ramps 55 of the coupling means 14 sliding along the cantilevers of the locking means 9. Hence, the locking means 9, i.e. the hooks 61, will be urged into engagement with the notches 58 and teeth 57 respectively of the guide nut 4, the locking means 9 pivoting in radial direction towards the centre of the assembly.

In the depicted position, the locking means 9 engage via their hooks 61 with the guide nut 4. In particular, the hooks 61 rest between the teeth 57 in respective notches 58. Moreover, in this position the hooks 61, especially the free ends of the cantilevers of the locking means 9 may be enclosed by sidewalls of the coupling means 14. This has the effect that a radial movement of the hooks 61 out of engagement with the teeth 57 and away from the guide nut 4 due to torsional moments is prevented in order to enable a secure engagement between the locking means 9 and the guide nut 4. In particular, torsional moments may occur during interaction with the guide nut 4 and a piston rod guided by the guide nut 4 during drug delivery or while trying to deliver a drug but having a blocked needle, which means an increased application of force.

In the position as depicted in FIG. 6C, the same effects occur as already explained with respect to FIG. 6A, i.e. rotational movement of the guide nut 4 with respect to the mounting device 10 is prevented. In this position which preferably may be taken during drug delivery, the guide nut 4 may urge a piston rod to be moved in a predetermined movement, i.e. a helical movement, thereby being threaded through the inner screw thread 8 of the guide nut 4 (see FIG. 4).

Moreover, as illustrated in FIG. 6C, the protrusion 56 of the coupling means 14 is now arranged on the other side of the protrusion 60 of the retaining means 62 of the mounting device 10 defining the engaged state as a discrete state (see also the general explanation in context of FIGS. 5A through 5C above).

Figure 6D:
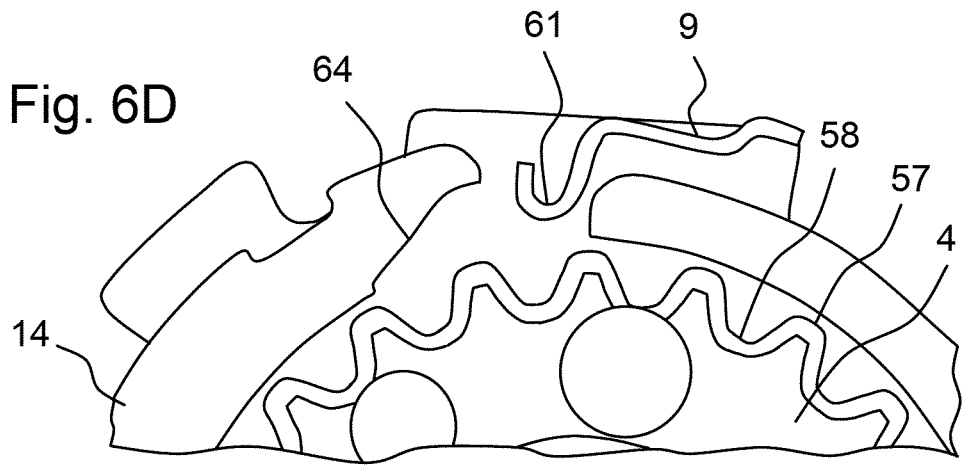
FIG. 6D shows a top view of a part of an assembled coupling means, guide nut and mounting device according to a third embodiment in the disengaged state.
Figure 6E:
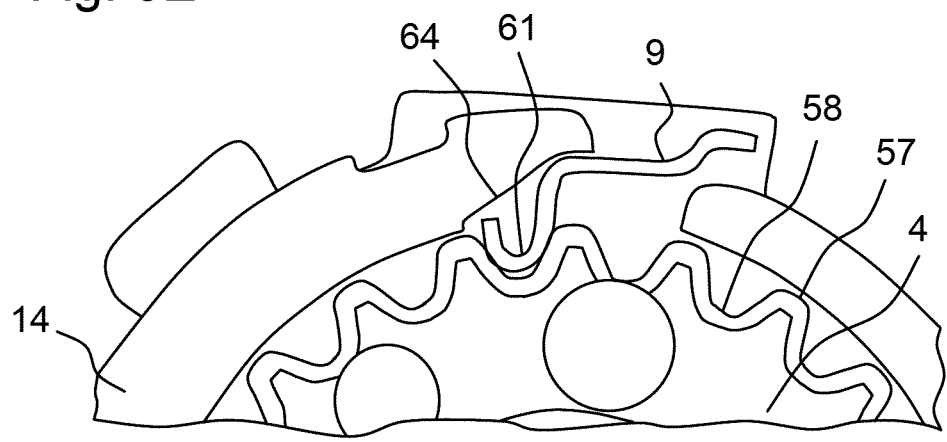
FIG. 6E shows a top view of a part of an assembled coupling means, guide nut and mounting device according to the embodiment of FIG. 6D in the engaged state.

The FIGS. 6D and 6E respectively show a top view of a part of an assembled coupling means 14, guide nut 4 and mounting device 10 according to a third embodiment in the disengaged state and the engaged state as well. The principle of the assembly according to FIGS. 6D and 6E is basically the same as explained in context with FIG. 6A. This means, the locking means 9 of the mounting device 10 are circumferentially arranged on at least a part of the exterior of the coupling means 14 and may pass radial recesses 53 of the coupling means 14 in order to engage with or disengage from the guide nut 4. According to this embodiment, a part of the interior of the coupling means 14 near the radial recess 53 is designed as a ramp 64 providing a transition from a narrowed diameter to a broader diameter of the interior of the coupling means 14 towards the radial recess 53 as explained below.

FIG. 6D shows the disengaged state, the hook 61 of the locking means 9 being out of engagement with a notch 58 and teeth 57 of the guide nut 4. FIG. 6E shows the engaged state, the hook 61 of the locking means 9 being in engagement with a notch 58 and teeth 57 of the guide nut 4.

The ramp 64 provides a kind of angled cut-out which smoothly receives at least a part of the locking means 9 (see FIG. 6E) and prevents the locking means 9 to scratch with a sharp edge of the free end of the hook 61 on the wall of the coupling means 14 and to damage the coupling means 14. In particular, torsional moments may occur on the guide nut 4 during interaction with a piston rod guided by the guide nut 4 during drug delivery or while trying to deliver a drug but having a bent or otherwise blocked needle, which means an increased application of force. These torsional moments may urge the locking means 9 and hooks 61 into radial movement away from the axis of the assembly. This movement does not lead to a disengagement of the locking means 9 from the guide nut 4, but provokes heavy contact forces between the locking means 9 and inner side walls of the coupling means 14. Due to the above explained angled ramp 64 of the coupling means 14 near the radial recess 53 of the coupling means 14, only a bent edge of the cantilever 9 and not the sharp edge of the hook 61 comes into contact with the inner side walls of the coupling means 14, the effect of heavy contact forces being notably attenuated and damage of the coulding means 14 being prevented.

Figure 7:
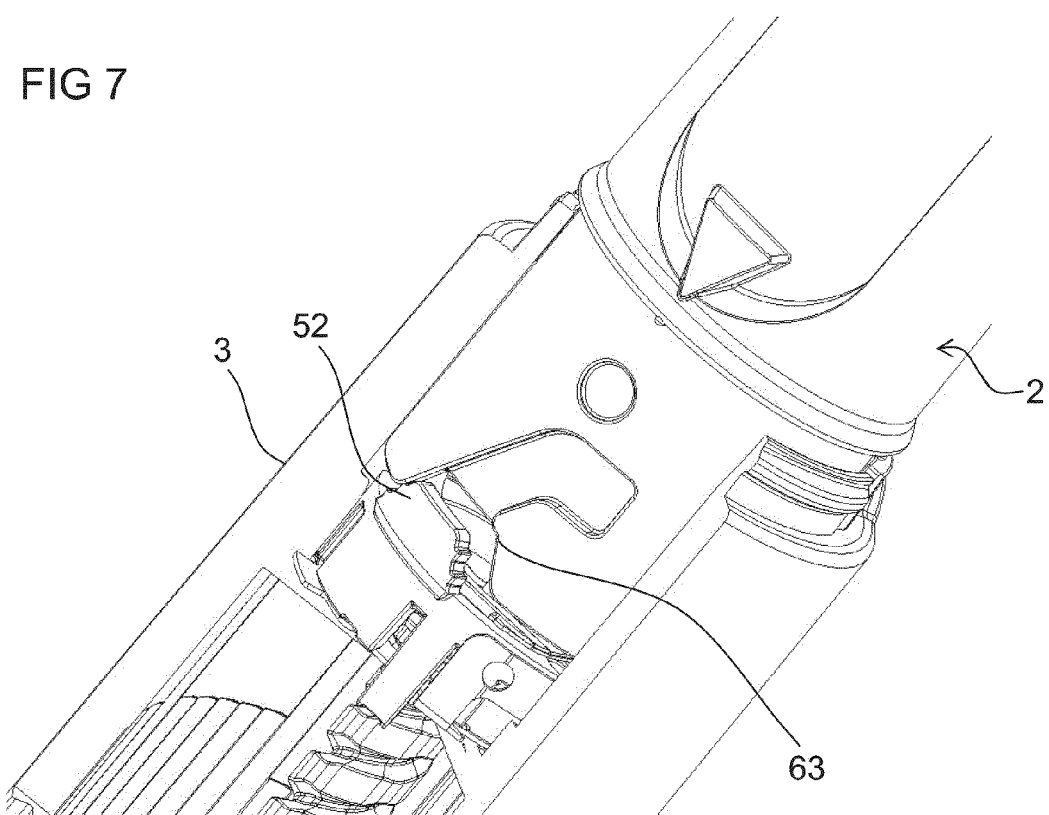
FIG. 7 shows a perspective view of a part of the drug delivery device with a cartridge holder being partially inserted into the drive assembly.

FIG. 7 shows a perspective view of a part of the drive assembly 1, i.e. the cartridge holder 2 and the housing 3, wherein the cartridge holder 2 is partially inserted into an opening of the housing 3 at a distal end of the housing 3. FIG. 7, furthermore, shows the assembly of the coupling means 14 and the mounting device 10 according to FIG. 6A, arranged within the housing 3. According to FIG. 7, the coupling means is in a position, wherein the locking means 9 is disengaged from the guide nut 4 as explained in the context of FIG. 6A.

With respect to FIG. 7, the cartridge holder 2 may be further moved into the housing 3 such that first fastening members 52 of the coupling means 14 as explained above and second fastening members 63 of the cartridge holder 2 may interact and engage with each other. This may effect a rotational movement of the coupling means 14 caused by a rotational movement of the cartridge holder 2 during mounting the cartridge holder 2 within the housing 3 of the drive assembly. Thus, the cartridge holder 2 may operate the coupling means 14 in order to switch the locking means 9 from the disengaged state to the engaged state as depicted in FIG. 6A via the coupling means 14 acting as an intermediary between the cartridge holder 2 and the locking means 9. By mounting a cartridge holder 2 with the housing 3, engagement of the locking means 9 of the mounting device 10 with the guide nut 4 may be enabled. Due to an engagement of the coupling means 14 with the cartridge holder 2, the coupling means 14 may be switched from the first position into the second position, wherein the first and second positions represent discrete and stable positions. Hence, the mechanism of rotationally fixing the guide nut 4 within the housing 3 according to the mechanism as explained above may be established in a secure and easy manner in order to prepare the drug delivery device for drug delivery. The cartridge holder 2 may provide fastening means like a thread, bayonet coupling or the like corresponding with respective fastening means arranged on the interior of the housing 3 for mounting the cartridge holder 2 to the housing 3.

Figure 8:
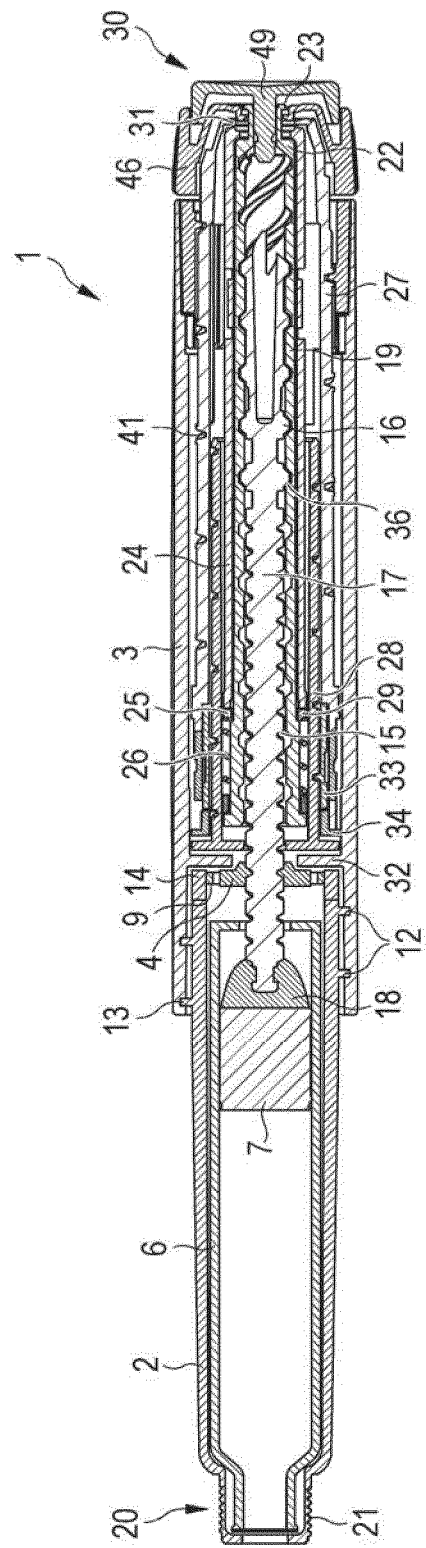
FIG. 8 shows a cross-section of an embodiment of the drug delivery device.

The drug delivery device will further be described in greater detail with regard to FIG. 8.

FIG. 8 shows a cross-section of an embodiment of the drug delivery device 1. The drug delivery device 1 comprises a body or housing 3 with a distal end 20 and a proximal end 30 and a removable cartridge holder 2 at the distal end 20. The housing 3 forms an exterior housing of the drug delivery device. The cartridge holder 2 is attached by a screw thread 12 mating a screw thread 13 of the main part of the housing 3. Other means of fastening the cartridge holder 2, like a bayonet joint, are not precluded. The cartridge holder 2 is provided for a cartridge 6 containing a drug. A piston or bung 7 is arranged in the cartridge 6 to be used to expel the drug. The distal end 20 may be provided with a nozzle 21, which can comprise a screw thread for the application of a needle assembly.

The drug delivery device 1 comprises a dosing mechanism, which includes a piston rod 17. The piston rod 17 has a distal end, which is nearest to the distal end 20 of the housing 3 and engages the bung 7 or a bearing 18 that is arranged between the bung 7 and the piston rod 17 to reduce damages that may be caused by friction. The piston rod 17 is movable in the distal direction, i. e. towards the distal end 20, by means of a drive device, the piston rod 17 pushing the bung 7 within the cartridge 6 in the distal direction to expel the drug from the cartridge 6 through the nozzle 21. A first screw thread 15 of the piston rod 17 is formed towards the distal end, and a second screw thread 16 of the piston rod 17 is formed nearer to the proximal end of the piston rod 17. The first screw thread 15 and the second screw thread 16 have opposite senses of rotation in this embodiment. One or both of these screw threads 15, 16 may comprise two or more single screw threads in helical alignment, forming a so-called multi-start thread, which is known per se from other mechanical devices.

The drive device comprises a drive sleeve 19, which forms a tube through which the piston rod 17 is moved. The drive sleeve 19 is generally cylindrical and provided with a bearing 22 carrying a radially extending flange 23 at the proximal end. The second screw thread 16 of the piston rod 17 is coupled with a corresponding screw thread on the inner wall of the drive sleeve 19 to guide a helical relative movement of the piston rod 17 with respect to the drive sleeve 19.

A generally cylindrical clutch 24 is disposed around the drive sleeve 19, and the clutch 24 is at least partially surrounded by a unit stop or end stop 28. The clutch 24 is located adjacent to the proximal end of the drive sleeve 19. Saw teeth 29 are arranged in azimuthal sequence at the distal end of the clutch 24, and further saw teeth 31 are arranged in azimuthal sequence at the proximal end of the clutch 24. The clutch 24 is keyed to the drive sleeve 19 by splines preventing a rotation of the clutch 24 relatively to the drive sleeve 19. The clutch 24 is provided with a plurality of flexible arms that engage a plurality of splines on an interior surface of a number sleeve or dose dial sleeve 27.

A clutch plate 25 and a biasing means 26 are located between the distal end of the clutch 24 and a radially extending flange at the distal end of the drive sleeve 19. The biasing means 26 may be a helical spring, for instance. The clutch plate 25 is rotationally locked to the housing 3. The proximal face of the clutch plate 25 is provided with saw teeth interacting with the saw teeth 29 at the distal end of the clutch 24 during the operation of dose setting.

The end stop 28 is disposed between the drive sleeve 19 and the dose dial sleeve 27. The end stop 28 is rotationally locked to the housing 3 and is free to move axially with respect to the housing 3. In this embodiment, the external surface of the end stop 28 is provided with a helical groove or thread, which is engaged with a threaded insert 33 of the dose dial sleeve 27. The insert 33 is retained within the dose dial sleeve 27 by means of an end cap 34, which is locked both rotationally and axially with respect to the dose dial sleeve 27. Splines of the end stop 28 may be provided to engage with the clutch plate 25, thus locking the clutch plate 25 rotationally with respect to the housing 3.

The dose dial sleeve 27 is provided with an outer helical thread 41 guiding a helical movement of the dose dial sleeve 27 with respect to the housing 3. A dose dial grip 46 is disposed at the proximal end 30 of the dose dial sleeve 27 and is provided with a central opening. A button 49 is provided at the proximal end 30 of the drug delivery device 1. The button 49 extends through the central opening of the dose dial grip 46 and enters the bearing 22 of the drive sleeve 19.

The first screw thread 15 of the piston rod 17 is guided by the screw thread 8 on the inner wall of the hole 5 of the guide nut 4. The guide nut 4 is prevented from axial movement with respect to the housing 3 by means of a web 32 and a part of the coupling means 14 (not shown in detail, see context of FIG. 6A). This means, a part of the coupling means 14 prevents axial movement of the guide nut 14 in distal direction, whereby the web 32 prevents axial movement of the guide nut 4 in proximal direction. The web 32 can be provided by interfaces or protruding elements formed by integral parts of the housing 3 extending transversely to the axis of the piston rod 17 into the interior volume of the housing 3. The web 32 can instead be formed by separate components that are fastened to the housing 3, e.g. by parts of the carrier 11 of the mounting device 10 (e.g. see FIG. 5A). The form of the web 32 is only restricted by its function to secure the guide nut 4 against an axial shift in proximal direction with respect to the housing 3. To this end, the web 32 comprises parts located on the proximal side of the guide nut 4, as can be seen from FIG. 8.

The locking means 9 can be mounted on the inner wall of the housing 3 or to an insert that is stationary with respect to the housing 3, e.g. the carrier 11 of the mounting device 10. The coupling means 14 is arranged such that it can operate the locking means 9 according to the principle explained in the context of FIG. 6A. In particular, the cartridge holder 2 may interact with the coupling means 14 such that the coupling means 14 may be rotated via a rotation of the cartridge holder 2, when the cartridge holder 2 is screwed to the housing 3 by means of the screw threads 12, 13. When the cartridge holder 2 is attached, the guide nut 4 is rotationally locked to the housing 3 by the engaged locking means 9. When the cartridge holder 2 is removed, the guide nut 4 is released and free to rotate relatively to the housing 3.

When the guide nut 4 is rotationally locked to the housing 3, the movement of the piston rod 17 is guided by the screw thread 8 of the guide nut 4 engaging the first screw thread 15 of the piston rod 17. The movement of the piston rod 17 is thus restricted to a helical movement relatively to the housing 3. When the guide nut 4 is not rotationally locked to the housing 3, the movement of the piston rod 17 is no longer restricted by the guide nut 4. As the guide nut 4 is still not able to move axially because of the coupling means 14 and the web 32, an axial shift of the piston rod 17 with respect to the housing 3 requires a corresponding helical movement with respect to the guide nut 4. This helical movement is easily generated, because the disengagement of the guide nut 4 from the locking means 9 enables the guide nut 4 to rotate freely and with low friction with respect to the housing 3 in a way to permit the movement of the piston rod 17.

The operation of the described embodiment of the drug delivery device will be described in the following.

To set a dose to be delivered, a user rotates the dose dial grip 46, thereby rotating the dose dial sleeve 27. The clutch 24 is engaged with the dose dial sleeve 27 by means of the saw teeth 31 at the proximal end of the clutch 24. This engagement and the splined engagement of the clutch 24 and the drive sleeve 19 make the clutch 24 and the drive sleeve 19 rotate with the dose dial sleeve 27. The clutch plate 25 is pushed towards the clutch 24 by the biasing means 26 in order to keep the saw teeth 29 of the clutch 24 and the saw teeth of the clutch plate 25 in contact. The profile of the saw teeth enables the relative movement of the clutch 24 and the clutch plate 25, which is rotationally locked to the housing 3, and this relative movement provides an audible and tactile feedback of the set operation. The setting of a unit or a specified subunit of a dose can thereby be indicated, if the saw teeth are dimensioned accordingly.

The larger the dose to be set, the farther the dose dial sleeve 27 is moved out of the housing 3. The relative movement of the dose dial sleeve 27 with respect to the housing 3 is helical, because the coupling is effected by means of a screw thread. The pitch of the outer helical thread 41 of the dose dial sleeve 27, the pitch of the second screw thread 16 of the piston rod 17, and the coupling between the dose dial sleeve 27 and the piston rod 17 are adapted to enable the helical movement of the dose dial sleeve 27 with respect to the housing 3 while leaving the piston rod 17 stationary with respect to the housing 3. The piston rod 17 is maintained at its position during the set operation, because the movement of the piston rod 17 is restricted by the engaged guide nut 4.

The end stop 28, which is coupled to the dose dial sleeve 27 but prevented from rotating with respect to the housing 3, moves in the proximal direction when the dose dial sleeve 27 is rotated out of the housing 3. When a dose is set equal to the remaining dispensable contents of the cartridge 6, the end stop 28 abuts a stop means 36 of the piston rod 17, which prevents the end stop 28 and simultaneously the dose dial sleeve 27 from moving further in the proximal direction, and the set operation is stopped.

If the set dose is too large, the set operation can be corrected by rotating the dose dial grip 46 in the opposite direction. The reverse rotation of the clutch 24 makes the saw teeth of the clutch 24 override the saw teeth of the clutch plate 25.

When the desired dose has been set, it can be dispensed by pressing the button 49 in the distal direction. This displaces the clutch 24 in the distal direction with respect to the dose dial sleeve 27, thereby decoupling the clutch 24 and simultaneously the drive sleeve 19 from the dose dial sleeve 27. The clutch 24 remains rotationally locked to the drive sleeve 19. The dose dial sleeve 27 is now free to move helically back in the distal direction without causing a rotational or helical movement of the drive sleeve. The displacement of the clutch 24 also moves the clutch plate 25 in the distal direction against the biasing means 26, until the clutch plate 25 abuts a shoulder on the drive sleeve 19. The clutch 24 and the clutch plate 25 are thereby engaged, so that a rotation of the clutch 24 relatively to the clutch plate 25 is prevented. A rotation of the clutch 24 and the drive sleeve 19 with respect to the housing 3 is thus also inhibited, because the clutch plate 25 is rotationally locked to the housing 3 by means of the end stop 28. The clutch plate 25, the clutch 24 and the drive sleeve 19 are moved together in the distal direction but do not rotate with respect to the housing 3.

The movement of the drive sleeve 19 causes a helical movement of the piston rod 17 with respect to the housing 3 by means of the second screw thread 16 engaging the inner screw thread of the drive sleeve 19. As the movement of the piston rod 17 is also guided by the first screw thread 15 engaging the inner screw thread 8 of the guide nut 4, and the guide nut 4 is presently engaged with the locking means 9 and thus rotationally locked to the housing 3, the helical movement of piston rod 17 advances the piston rod 17 in the distal direction. The ratio of the pitches of the first screw thread 15 and the second screw thread 16 can be selected according to a desired proportion between the distance by which the drive sleeve 19 is shifted and the distance by which the piston rod 17 is shifted relatively to the housing 3 during the dispense operation. The movement of the dose dial sleeve 27 in the distal direction causes the end stop 28 to move back to its initial position within the housing 3.

When the cartridge 6 is empty, it may be substituted with a new one. For this purpose, the cartridge holder 2 is removed from the housing 3, the empty cartridge 6 is taken out of the cartridge holder 2, and a new cartridge is inserted. Before the cartridge holder 2 is attached to the housing 3, the piston rod 17 is reset to a start position, which is appropriate in view of the location that is occupied by the bung 7 when the cartridge holder 2 is attached, which means the piston rod 17 is moved backwards in proximal direction.

The piston rod 17 is reset in the proximal direction. The movement of the piston rod 17 is restricted by the first screw thread 15 and the second screw thread 16 engaging the guide nut 4 and the drive sleeve 19, respectively. When both the guide nut 4 and the drive sleeve 19 are stationary with respect to the housing 3, a movement of the piston rod 17 relatively to the housing 3 is not possible because the first screw thread 15 and the second screw thread 16 do not have the same pitch and sense of rotation. The reset of the piston rod 17 by an axial movement in the proximal direction is possible when the guide nut 4 is free to rotate relatively to the housing 3, thus enabling a helical movement of the guide nut 4 with respect to the piston rod 17 irrespective of the position and movement of the piston rod 17 with respect to the housing 3.

The reset operation is therefore made possible by a release of the guide nut 4. As the coupling means 14 is operated by the cartridge holder 2, the locking means 9 is disengaged from the guide nut 4 due to interaction with the coupling means 14, as long as the cartridge holder 2 is not attached to the housing 3. When the piston rod 17 is shifted in the proximal direction, the guide nut 4 rotates according to the required helical movement of the guide nut 4 with respect to the piston rod 17. When the piston rod 17 is reset, the cartridge holder 2 is attached to the housing 3. The coupling means 14 is rotated via a rotational mounting movement of the cartridge holder 2 (see FIG. 7) and enables the locking means 9 to engage with the guide nut 4, so that the guide nut 4 is rotationally locked to the housing 3. The drug delivery device is then ready for further operation as described above.

The reset of the piston rod 17 can be performed manually, while the cartridge holder 2 stays completely removed. The reset can be achieved by pushing the piston rod 17 towards the proximal end 30 or by holding the device with the proximal end 30 pointing down to have the gravitational force move the piston rod 17 to the reset position. Instead, the piston rod 17 can be pushed by the bung 7 to the reset position, when the cartridge holder 2 is being attached and approaches the proximal end 30.

If the cartridge holder 2 is provided with a screw thread 12, it approaches the proximal end 30 slowly and steadily with every turn of the cartridge holder 2 with respect to the housing 3 in the course of the attachment. The helical movement of the cartridge holder 2 with respect to the housing 3, generated by a screw thread, has the advantage of not building up a load on the bung 7, which might shift the bung 7 before the drug delivery device 1 is used. If the cartridge holder 2 is provided with a bayonet coupling and there is no screw thread to control the smooth attachment of the cartridge holder 2, the reset of the piston rod 17 can be supported by means preventing a premature shift of the bung 7 towards the distal end 20.

An embodiment of the drug delivery device was described in detail in conjunction with FIG. 8, in order to make the drive assembly completely clear. The details of this embodiment in their entirety do not represent the essential features of the disclosure and do not restrict the scope of the disclosure as claimed. Various modifications, alterations and substitutions of the drive assembly and the drug delivery device are within the scope of the disclosure.

The drug delivery device has many advantages, among them the enablement of an easy replacement of the cartridge and a particularly easy reset of the piston rod. The reset operation thus need not be affected by details of the drive mechanism concerning the operations of setting and dispensing. The piston rod can therefore be provided with various functions and realized in various different embodiments, all of them enabling the reset operation as described. The drive assembly according to the disclosure renders the reset operation independent of the other operations of the drive mechanism and the piston rod.

The invention claimed is:

1. A drive assembly for a drug delivery device, the drive assembly being connectable with a cartridge holder and comprising:
    a housing
    a piston rod, the piston rod being movable in a distal direction for drug delivery,
    a guide nut, the guide nut being rotatable relative to the housing around an axis of the assembly and provided for guiding the piston rod,
    a locking means, the locking means being enabled to take an engaged state in which the locking means is engaged with the guide nut in order to prevent rotation of the guide nut and to take a disengaged state in which the locking means is disengaged from the guide nut in order to allow rotation of the guide nut, and
    a coupling means, the coupling means being rotatable relative to the housing around the axis of the assembly for interaction with the locking means in order to change between the engaged state and the disengaged state of the locking means,
    wherein the coupling means comprises one or more retaining means for preventing axial movement of the coupling means with respect to the housing.

2. The drive assembly according to claim 1, wherein the coupling means is rotatable between a first position and a second position, wherein in the first position the coupling means prevents engagement of the locking means with the guide nut and wherein in the second position the coupling means allows engagement of the locking means with the guide nut.

3. The drive assembly according to claim 1, wherein the locking means engaged with the guide nut for moving the piston rod in the distal direction during drug delivery and wherein the locking means is disengaged from the guide nut for enabling a reset operation, thereby moving the piston rod in a proximal direction opposite to the distal direction, the guide nut being enabled to rotate relative to the housing.

4. The drive assembly according to claim 1, wherein the coupling means provides one or more first fastening members for engagement with one or more corresponding second fastening members of a cartridge holder, the coupling means being rotatable by actuation of the first fastening members.

5. The drive assembly according to claim 1, wherein the guide nut is at least partially encompassed by the coupling means and the locking means, wherein the locking means interacts with the guide nut when the locking means moves in radial direction towards the axis of the assembly.

6. The drive assembly according to claim 5, wherein the coupling means is designed as a ring-shaped member, providing one or more radial recesses, the locking means being circumferentially arranged on at least a part of the exterior of the coupling means and provided for passing the recesses of the coupling means in order to engage with the guide nut.

7. The drive assembly according to claim 5, wherein the coupling means is designed as a ring-shaped member, providing one or more radial recesses and being circumferentially arranged on at least a part of the exterior of the locking means, the locking means being provided for at least partially passing the recesses of the coupling means in order to disengage from the guide nut.

8. The drive assembly according to claim 7, wherein a part of the interior of the coupling means near the one or more radial recesses is designed as a ramp providing a transition from a narrowed diameter to a broader diameter of the interior of the coupling means towards the one or more radial recesses.

9. The drive assembly according to claim 1, wherein the coupling means comprises one or more retaining means for preventing axial movement of the coupling means with respect to the housing.

10. The drive assembly according to claim 1, wherein the locking means comprises two members arranged on opposite sides of a carrier, wherein the carrier is rotationally fixed with respect to the housing.

11. The drive assembly according to claim 1, wherein the guide nut is a toothed wheel having notches between the teeth, and wherein the locking means is at least one resilient or resiliently mounted cantilever comprising a hook for engagement with the notches of the guide nut.

12. The drive assembly according to claim 1, wherein the free end of the cantilever provides a sinusoidal shape with at least two reverse loops, wherein a first loop is molded towards the axis of the assembly and forms the hook and wherein a second loop is molded away from the axis of the assembly and finishes in the free end of the cantilever, the second loop being designed to at least partially contact with a part of the coupling means in the engaged state of the locking means.

13. The drive assembly according to claim 1, wherein the guide nut comprises a screw thread for coupling the piston rod and enabling a helical movement of the piston rod relative to the guide nut.

14. A drug delivery device comprising a drive assembly according to claim 1 and a cartridge holder, the cartridge holder being releasably mounted on a distal end of the assembly and being engaged with the coupling means, the coupling means interacting with the locking means such that the locking means is in the engaged state when the cartridge holder is assembled to the drive assembly.

15. A drug delivery device according to claim 14, having a shape of an injection pen.

\* \* \* \* \*